(12) United States Patent
Pallett et al.

(10) Patent No.: US 6,887,829 B2
(45) Date of Patent: May 3, 2005

(54) HERBICIDAL COMPOSITIONS

(75) Inventors: Ken Pallett, Königstein (DE); Ashley Slater, Ongar (GB)

(73) Assignee: Bayer CropScience S.A., Lyons (FR)

( * ) Notice: Subject to any disclaimer, the term of this patent is extended or adjusted under 35 U.S.C. 154(b) by 0 days.

(21) Appl. No.: 10/380,353

(22) PCT Filed: Sep. 17, 2001

(86) PCT No.: PCT/EP01/10695

§ 371 (c)(1),
(2), (4) Date: Oct. 2, 2003

(87) PCT Pub. No.: WO02/21920

PCT Pub. Date: Mar. 21, 2002

(65) Prior Publication Data

US 2004/0053784 A1 Mar. 18, 2004

(30) Foreign Application Priority Data

Sep. 18, 2000 (GB) .............................. 0022932

(51) Int. Cl.$^7$ ................... A01N 35/06; A01N 41/10; A01N 43/66; A01N 43/68; A01N 43/70
(52) U.S. Cl. .................................... 504/133
(58) Field of Search ....................... 504/133

(56) References Cited

U.S. PATENT DOCUMENTS

| | | | |
|---|---|---|---|
| 4,937,386 A | * | 6/1990 | Ueda et al. ............. 504/348 |
| 4,968,342 A | | 11/1990 | Forster et al. |
| 5,506,195 A | | 4/1996 | Ensminger et al. |
| 6,046,134 A | * | 4/2000 | De Gennaro et al. ....... 504/133 |

FOREIGN PATENT DOCUMENTS

| | | |
|---|---|---|
| DE | 42 16 880 A1 | 11/1993 |
| EP | 0 186 118 A2 | 7/1986 |
| EP | 0 348 737 A1 | 1/1990 |
| IT | 1224249 B1 | 9/1990 |
| JP | 07 010713 A1 | 1/1995 |
| WO | WO-95/28839 | 11/1995 |
| WO | WO-96/13163 | 5/1996 |
| WO | WO-96/17519 | 6/1996 |
| WO | WO-00/166727 | 3/2000 |

OTHER PUBLICATIONS

Derwent English Language abstract of DE 42 16 880 A1.
Derwent English Language abstract of JP 07010713A.
Derwent English Language abstract of IT 1224249.

* cited by examiner

Primary Examiner—S. Mark Clardy
(74) Attorney, Agent, or Firm—Connolly Bove Lodge & Hutz LLP

(57) ABSTRACT

The invention relates to a method for controlling the growth of weeds at a locus which comprises applying to said locus: (a) 2-(2'-nitro-4'-methylsulfonylbenzoyl)-1,3-cyclohexanedione, or an agriculturally acceptable salt or metal complex thereof; and (b) a triazine herbicide with the exclusion of atrazine; and their use as herbicides.

14 Claims, No Drawings

HERBICIDAL COMPOSITIONS

The present patent application is a 371 of PCT/EP01/10695 filed on Sep. 17, 2001 and claims priority to United Kingdom patent application number 0022932.8, filed on Sep. 18, 2000, under 35 U.S.C. 119.

This invention relates to new herbicidal compositions comprising a mixture of a benzoyl cyclohexanedione and herbicidal 1,3,5-triazine or 1,2,4-triazinone compounds. It also relates to the use of the mixture per se and to a method of controlling weeds.

The above compounds are already known in the art as herbicides. 1,3,5-Triazine and 1,2,4-triazinone herbicides (hereinafter referred to as the triazine herbicides) are well known in the art and include ametryn ($N^2$-ethyl-$N^4$-isopropyl-6-methylthio-1,3,5-triazine-2,4-diamine), atrazine (6-chloro-$N^2$-ethyl-$N^4$-isopropyl-1,3,5-triazine-2,4-diamine), aziprotryne (4-azido-N-isopropyl-6-methylthio-1,3,5-triazin-2-ylamine), cyanazine [2-(4-chloro-(ethylamino)1,3,5-triazin-2-ylamino)-2-methylpropionitrile], methoprotryne [$N^2$-isopropyl-$N^4$-methoxypropyl)-6-methylthio-1,3,5-triazine-2,4-diamine], metribuzin (4-amino-6-tert-butyl-3-methylthio-1,2,4-triazin-5(4H)-one), prometryn ($N^2$,$N^4$-di-isopropyl-6-methylthio-1,3,5-triazine-2,4-diamine), prometon ($N^2$,$N^4$-di-isopropyl-6-methoxy-1,3,5-triazine-2,4-diamine), propazine (6-chloro-$N^2$,$N^4$-di-isopropyl-1,3,5-triazine-2,4-diamine), simetryn ($N^2$,$N^4$-diethyl-6-methylthio-1,3,5-triazine-2,4-diamine), simazine (6-chloro-$N^2$,$N^4$-diethyl-1,3,5-triazine-2,4-diamine), terbuthylazine ($N^2$-tert-butyl-6-chloro-$N^4$-ethyl-1,3,5-triazine-2,4-diamine), terbutryn ($N^2$-tert-butyl-$N^4$-ethyl-6-methylthio-1,3,5-triazine-2,4-diamine) and trietazine (6-chloro-$N^2$,$N^2$,$N^4$-triethyl-1,3,5-triazine-2,4-diamine), and are disclosed for example in "The Pesticide Manual", 12th edition, 2000 (British Crop Protection Council) and earlier editions, as selective herbicides. Herbicidal 4-benzoylisozaxoles of formula (I) below are disclosed in European Patent (Application) Publications No. 0418175, 0487357, 0527036 and 0560482.

Herbicidal benzoyl cyclohexanediones are disclosed in the literature, for example European Patent Publication No. 0186118. In particular U.S. Pat. No. 5,506,196 discloses 2-(2'-nitro-4'-methyl sulfonylbenzoyl)-1,3-cyclohexanedione.

It has been found that the use of triazine herbicides in combination with certain benzoyl cyclohexan dione derivatives, extends the spectrum of herbicidal activity without loss of crop selectivity. Therefore the said combinations represent an important technological advance. The term "combination" as used in this specification refers to the "combination" of a benzoyl cyclohexanedione herbicide and a triazine herbicide.

The invention also seeks to provide a herbicidal composition which allows lower dose rates of triazine herbicides to be applied to the environment without reducing (and preferably increasing) the level of weed control.

The present invention provides a method for controlling the growth of weeds (i.e. undesired vegetation) at a locus which comprises applying to the locus a herbicidally effective amount of:

(a) a benzoyl cyclohexanedione of formula (I):

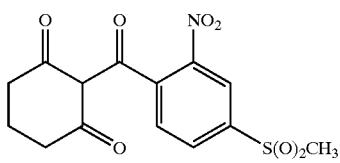

which is 2-(2'-nitro-4'-methylsulfonylbenzoyl)-1,3-cyclohexanedione, or an agriculturally acceptable salt or metal complex thereof; and (b) a triazine herbicide with the exclusion of atrazine.

The triazine herbicide and benzoyl cyclohexanedione are normally used in the form of herbicidal compositions (i.e. in association with compatible diluents or carriers and/or surface-active agents suitable for use in herbicidal compositions), for example as hereinafter described.

Preferably the triazine herbicide is a compound of the formula (II):

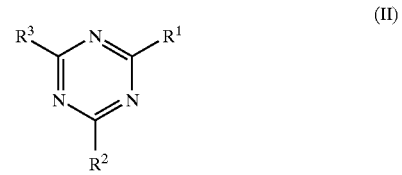

wherein $R^1$ represents chlorine or straight- or branched chain alkylthio or alkoxy having from one to six carbon atoms; $R^2$ represents azido, monoalkylamino, dialkylamino or cycloalkylamino, in which the alkyl or cycloalkyl moieties may be optionally substituted by one or more substituents selected from cyano and alkoxy; and $R^3$ represents straight- or branched-chain N-alkylamino having from one to six carbon atoms;
or of formula (III):

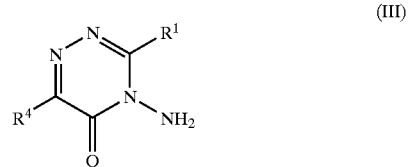

wherein $R^1$ is as defined above and $R^4$ represents straight- or branched chain alkyl having from one to six carbon atoms.

More preferably $R^1$ represents chlorine or methylthio and $R^3$ represents straight- or branched-chain N-alkylamino having from one to four carbon atoms.

Compositions containing compounds of formula (II) above wherein $R^2$ represents azido, straight- or branched-chain N-alkylamino having from one to four carbon atoms (wherein th alkyl moiety is optionally substituted by cyano or methoxy) are preferred.

Further preferred compounds of formula (II) above are those in which $R^3$ represents N-(t-butyl)amino, $R^2$ represents N-ethylamino and $R^1$ represents chlorine or methylthio, which are known respectively as terbuthylazine and terbutryn.

Preferred compounds of formula (II) above are those in which $R^1$ represents chlorine, $R^3$ represents N-ethylamino and $R^2$ represents N-ethylamino or N-(2-methylpropanenitrile)amino, known respectively as simazine and cyanazine; cyanazine being most preferred.

A preferred compound of formula (III) above is the compound in which $R^1$ represents methylthio, $R^4$ represents tert-butyl, which is known as metribuzin.

The amounts of the triazine herbicide and benzoyl cyclohexanedione applied vary depending on the the weeds present and their population, the compositions used, the timing of the application, the climatic and edaphic conditions, and (when used to control the growth of weeds in crop growing areas) the crop to be treated. In general, taking these factors into account, application rates from 5 g to 500 g of benzoyl cyclohexanedione and from 250 g to 5000 g of the triazine herbicide per hectare give good results. However, it will be understood that higher or lower application rates may be used, depending upon the problem of weed control encountered.

For the selective control of weeds at a locus of weed infestation which is an area used, or to be used, for growing of crops application rates from 5 g to 500 g of benzoyl cyclohexanedione and from 250 g to 5000 g of the triazine herbicide per hectare are particularly suitable, preferably from 25 to 150 g of benzoyl cyclohexanedione and from 500 g to 1500 g of the triazine herbicide per hectare. When applied to a crop-growing area, the rate of application should be sufficient to control the growth of weeds without causing substantial permanent damage to the crop.

The combined use described abov may be used to control a very wide spectrum of annual broad-leafed weeds and grass weeds in crops, e.g. maize and plantatation crops such as sugar cane, without significant permanent damage to the crop. The combined use described above offers both foliar and residual activity and consequently can be employed over a long period of crop development, i.e. from pre-weed pre-crop emergence to post-weed post-crop emergence.

In the method according to this feature of the present invention the combined use of (a) and (b) to control grass weeds in maize is preferred.

Where the triazine herbicide is ametryn the combined use of (a) and (b) to control grass weeds in sugar cane is also preferred.

In the method described above, the combined use of (a) and (b) in proportions of 2:1 to 1:1000 wt/wt of (a): (b) is preferred, proportions of 1:3 to 1:60 wt/wt (or 1:3.3 to 1:60 wt/wt) being particularly preferred.

By the term 'pre-emergence application' is meant application to the soil in which the weed seeds or seedlings are present before emergence of the crop. By the term 'post-emergence application' is meant application to the aerial or exposed portions of the weeds which have emerged above the surface of the soil. By the term 'foliar activity' is meant herbicidal activity produced by application to the aerial or exposed portions of the weeds which have emerged above the surface of the soil. By the term 'residual activity' is meant herbicidal activity produced by application to the soil in which weed seeds or seedlings are present before emergence of the weeds above the surface of the soil, whereby seedlings present at the time of application or which germinate subsequent to application from seeds present in the soil, are controlled.

In the present invention, PPI or pre-emergence applications are preferred, and pre-emergence application of the benzoyl cyclohexanedione and triazine herbicide is most preferred.

Preferably the combination of benzoyl cyclohexanedione and triazine herbicide is applied to an area used, or to be used, for the growing of a crop, for example maize, sugarcane or plantation crops. Preferably the crop is maize.

In accordance with the usual practice, a tank mix may be prepared prior to use by combining separate formulations of the individual herbicidal components.

The following non-limiting experiments illustrate the present invention.

EXAMPLE 1

Seed of various broad-leaf and grass weed species were sown in unsterilised clay loam soil. The soil surface was then sprayed with ranges of concentrations of either the individual herbicide or mixtures of two herbicides in various proportions dissolved in a mixture of acetone and water. The said weeds are *Amaranthus retroflexus, Setaria viridis, Setaria faberi* and *Echinochloa crus-galli.*

Two weeks after treatment the percent reduction in plant growth, compared to an untreated control, was assessed.

Control in one or more weed species was observed by combinations of the present invention.

EXAMPLE 2

Seed of various weed species, as listed in Example 1, were sown and grown up to a 1–3 leaves stage. Post-emergence applications of a range of concentrations of either the individual herbicide or mixtures of two herbicides in various proportions dissolved in a mixture of acetone and water were made.

Two weeks after treatment the percent reduction in plant growth, compared to an untreated control, was assessed.

Control in one or more weed species was observed by combinations of the present invention.

According to a further feature of the present invention there are provided herbicidal compositions comprising:

(a) 2-(2'-nitro-4'-methylsulfonylbenzoyl)-1,3-cyclohexanedione, or an agriculturally acceptable salt or metal complex thereof; and (b) a triazine herbicide with the exclusion of atrazine;

in association with, and preferably homogeneously dispersed in, a herbicidally acceptable diluent or carrier and/or surface active agent.

The term "herbicidal composition" is used in a broad sense, to include not only compositions which are ready for use as herbicides but also concentrates which must be diluted before use. Preferably, the compositions contain from 0.05 to 90% by weight of benzoyl cyclohexanedione and triazine herbicide.

Unless otherwise stated, the percentages and ratios appearing in this specification are by weight.

Generally a composition in which the ratio of (a):(b) is from 1:6000 to 64:1 wt/wt of (a):(b) is used, proportions from 1:600 to 4:1 wt/wt (or from 1:600 to 3.41:1 wt/wt) being preferred, with proportions from 1:100 to 2:1 wt/wt (or from 1:100 to 1.33:1 wt/wt) particularly preferred and proportions of from 1:20 to 1:1 wt/wt (or from 1:20 to 1:1.33 wt/wt) especially preferred.

The herbicidal composition may contain solid and liquid carriers and surface-active agents (e.g. wetters, dispersants or emulsifiers alone or in combination). Surface-active agents that may be present in the herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric add esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, absorbent carbon black and clays such as kaolin and bentonite. Examples of suitable liquid diluents include water, acetophenone, cyclohexanone, isophorone, toluene, xylene, and mineral, animal, and vegetable oils (these diluents may be used alone or in combination).

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

The wettable powders (or powders for spraying) usually contain from 20 to 95% of benzoyl cyclohexanedione and triazine herbicide, and they usually contain, in addition to the solid vehicle, from 0 to 5% of a wetting agent, from 3 to 10% of a dispersant agent and if necessary, from 0 to 10% of one or more stabilisers and/or other additives such as penetrating agents, adhesives or anti-caking agents and colourings.

The aqueous suspension concentrates, which are applicable by spraying, are prepared in such a way as to obtain a stable fluid product (by fine grinding) which does not settle out and they usually contain from 10 to 75% of benzoyl cyclohexanedione and triazine herbicide, from 0.5 to 15% of surface acting agents, from 0.1 to 10% of thixotropic agents, from 0 to 10% of suitabl additives such as antifoams, corrosion inhibitors, stabilisers, and water or an organic liquid in which the active substance is sparingly soluble or insoluble. Some organic solid substances or inorganic salts can be dissolved in order to assist in preventing sedimentation or as antifreeze for the water.

Preferred herbicidal compositions according to the present invention are wettable powders and water-dispersible granules.

Herbicidal compositions according to the present invention may also comprise a benzoyl cyclohexanedione and triazine herbicide in association with, and preferably homogeneously dispersed in, one or more other pesticidally active compounds and, if desired one or more compatible pesticidally acceptable diluents and carriers. Preferred herbicidal compositions according to the present invention are those which comprise a benzoyl cyclohexanedione and a triazine herbicide in association with other herbicides.

The compositions of the invention may be made up as an article of manufacture comprising a benzoyl cyclohexanedione and a triazine herbicide and optionally other pesticidally active compounds as hereinbefore described, and as is preferred, a herbicidal composition as hereinbefore described and preferably a herbicidal concentrate which must be diluted before use, comprising the benzoyl cyclohexanedione and triazine herbicide within a container for the aforesaid benzoyl cyclohexanedione and triazine herbicide or a said herbicidal composition and instructions physically associated with the aforesaid container, setting out the manner in which the aforesaid benzoyl cyclohexanedione and triazine herbicide or herbicidal composition contained therein, is to be used to control the growth of weeds. The containers will normally be of the types conventionally used for the storage of chemical substances and concentrated herbicidal compositions, which are solids or liquids at normal ambient temperatures, for example cans and drums of plastics materials or metal (which may be internally-lacquered), bottles of glass and plastics materials; and when the contents of the container is a solid, for example a granular herbicidal composition, boxes, for example of cardboard, plastics material, metal or sacks. The containers will normally be of sufficient capacity, to contain amounts of the active ingredients or herbicidal compositions suffici nt to treat at least one hectare of ground, to control the growth of weeds therein but will not exceed a size which is convenient for conventional methods of handling. Instructions will be physically associated with the container, for example by being printed directly thereon or on a label or tag affixed thereto. The directions will normally indicate that the contents of the container, after dilution if necessary, are to be applied to control the growth of weeds at rates of application from 0.5 to 512 g of benzoyl cyclohexanedione and from 8 to 3000 g of triazine herbicide per hectare in the manner and for the purpose hereinbefore described.

The process described in U.S. Pat. No. 5,006,158 may be used to prepare the benzoyl cyclohexanedione of formula (I).

According to a further feature of the present invention, there is provided a product comprising:

(a) 2-(2'-nitro-4'-methylsulfonylbenzoyl)-1,3-cyclohexanedione or an agriculturally acceptable salt or metal complex thereof; and (b) a triazine herbicide with the exclusion of atrazine;

as a combined preparation for simultaneous, separate or sequential use in controlling the growth of weeds at a locus.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for controlling the growth of weeds at a locus which comprises applying to said locus:

(a) 2-(2'-nitro-4'-methylsulfonylbenzoyl)-1,3-cyclohexanedione, or an agriculturally acceptable salt or metal complex thereof, and (b) a triazine herbicide with the exclusion of (i) atrazine or (ii) any triazine belonging to the group of sulfonylureas.

2. A method according to claim 1 wherein the triazine herbicide is a compound of the formula (II):

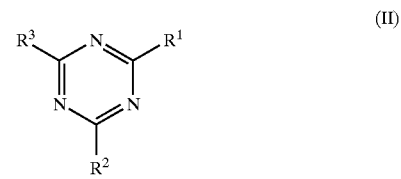

(II)

wherein $R^1$ represents chlorine or straight- or branched chain alkylthio or alkoxy having from one to six carbon atoms; $R^2$ represents azido, monoalkylamino, dialkylamino or cycloalkylamino, in which the alkyl or cycloalkyl moieties may be optionally substituted by one or more substituents selected from cyano and alkoxy; and $R^3$ represents straight- or branched-chain N-alkylamino having from one to six carbon atoms;

or of formula (III):

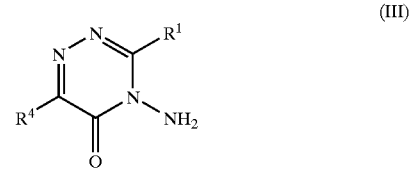

(III)

wherein $R^1$ is as defined above and $R^4$ represents straight- or branched chain alkyl having from one to six carbon atoms.

3. A method according to claim 2, wherein in formula II, $R^2$ represents azido or straight- or branched- chain N-alkylamino having from one to four carbon atoms, wherein the alkyl moiety is optionally substituted by cyano or methoxy.

4. A method according to claim 1, wherein the triazine herbicide is selected from: simazine, which is 6-chloro-$N^2$, $N^4$-diethyl-1,3,5-triazine-2,4-diamine; and cyanazine, which is 2-(4-chloro-6-ethylamino-1,3,5-triazin-2-ylamino)-2-methylpropionitrile.

5. A method according to claim 4 wherein the triazine herbicide is cyanazine.

6. A method according to claim 1, wherein the triazine herbicide is metribuzin, which is 4-amino-6-tert-butyl-3-methylthio-1,2,4-triazin-5(4H)-one.

7. A method according to claim 1, in which the application rate of benzoyl cyclohexanedione is from 5 g to 500 g per hectare and the application rate of triazine herbicide is from 250 g to 5000 g per hectare.

8. A method according to claim 1, in which the application rate of benzoyl cyclohexanedione is from 25 g to 150 g per hectare and the application rate of triazine herbicide is from 500 g to 1500 g per hectare.

9. A method according to claim 1, wherein (a) and (b) are applied to the locus for the control of grass weeds in maize.

10. A method according to claim 1, wherein (a) and (b) are applied to the locus pre-emergence of the weeds.

11. A herbicidal composition comprising:
(a) 2-(2'-nitro-4'-methylsulfonylbenzoyl)-1,3-cyclohexanedione, or an agriculturally acceptable salt or metal complex thereof, and
(b) a triazine herbicide with the exclusion of (i) atrazine or (ii) any triazine belonging to the group of sulfonylureas;

in association with a herbicidally acceptable diluent or carrier and/or surface active agent.

12. A herbicidal composition according to claim 11 wherein the ratio of (a):(b) is from 2:1 to 1:1000 wt/wt.

13. A herbicidal composition according to claim 11, in which the ratio of (a):(b) is from 1:4 to 1:60 wt/wt.

14. A product comprising (a) 2-(2'-nitro-4'-methylsufonylbenzoyl)-1,3-cyclohexanedione, or an agriculturally acceptable salt or metal complex thereof, and (b) a triazine herbicide with the exclusion of atrazine or any triazine belonging to the group of sulfonylureas, as a combined preparation for simultaneous, separate or sequential use in controlling the growth of weeds at a locus.

* * * * *

UNITED STATES PATENT AND TRADEMARK OFFICE
CERTIFICATE OF CORRECTION

PATENT NO. : 6,887,829 B2
DATED : May 3, 2005
INVENTOR(S) : Ken Pallett et al.

It is certified that error appears in the above-identified patent and that said Letters Patent is hereby corrected as shown below:

Title page,
Item [73], Assignee, delete "Lyons" and insert -- Lyon --.

Signed and Sealed this

Eighteenth Day of October, 2005

JON W. DUDAS
*Director of the United States Patent and Trademark Office*